United States Patent
Fregoso (10) Patent No.: US 7,535,184 B1
(45) Date of Patent: May 19, 2009

(54) PHOTOPOLYMERIZATION APPARATUS

(75) Inventor: Gilbert Fregoso, Hamilton, MT (US)

(73) Assignee: Design Rite LLC, Walnut, CA (US)

( * ) Notice: Subject to any disclaimer, the term of this patent is extended or adjusted under 35 U.S.C. 154(b) by 613 days.

(21) Appl. No.: 11/135,832

(22) Filed: May 23, 2005

Related U.S. Application Data (63) Continuation-in-part of application No. 10/647,028, filed on Aug. 22, 2003, now abandoned, which is a continuation of application No. 09/907,140, filed on Jul. 17, 2001, now Pat. No. 6,611,110, which is a continuation-in-part of application No. 09/765,897, filed on Jan. 16, 2001, now Pat. No. 6,724,156.

(51) Int. Cl.
*G05F 1/00* (2006.01)

(52) U.S. Cl. .................. 315/291; 315/224; 315/225; 315/360; 362/800; 362/294; 433/27; 433/29

(58) Field of Classification Search .................. 315/112, 315/115, 117, 224, 225, 291, 292, 294, 307, 315/360, 362; 362/119, 231, 293, 294, 800; 433/27, 29, 31
See application file for complete search history.

(56) References Cited

U.S. PATENT DOCUMENTS

| | | | |
|---|---|---|---|
| 4,384,317 A | 5/1983 | Stackpole | |
| 4,625,119 A | 11/1986 | Murdock, III | |
| 4,740,706 A | 4/1988 | Murdock, III | |
| 4,973,847 A | 11/1990 | Lackey et al. | |
| 5,233,283 A | 8/1993 | Kennedy | |
| 5,312,249 A | 5/1994 | Kennedy | |
| 5,420,768 A | 5/1995 | Kennedy | |
| 5,614,151 A | 3/1997 | LeVay et al. | |
| 5,634,711 A | 6/1997 | Kennedy et al. | |
| 5,756,981 A | 5/1998 | Roustaei et al. | |
| 5,765,940 A | 6/1998 | Levy et al. | |
| 5,896,093 A | 4/1999 | Sjobom | |
| 5,912,470 A | 6/1999 | Eibofner et al. | |
| 5,914,865 A | 6/1999 | Barbehenn et al. | |
| 5,922,605 A | 7/1999 | Feurstein et al. | |
| 6,078,148 A | 6/2000 | Hochstein | |
| 6,095,812 A | 8/2000 | Senn et al. | |
| 6,102,696 A | 8/2000 | Osterwalder et al. | |
| 6,103,203 A | 8/2000 | Fischer | |

(Continued)

FOREIGN PATENT DOCUMENTS

EP      0 567 280 A2      4/1993

OTHER PUBLICATIONS

Sherman, Len, Logic Power Drivers High-Intensity LEDs, Ideas for Design, Oct. 23, 1997, 142 and 144, vol. 2328.

(Continued)

*Primary Examiner*—Haissa Philogene
(74) *Attorney, Agent, or Firm*—Jean Kyle (57) ABSTRACT

A light-weight, portable photocuring device possesses a single light emitting diode (LED). The single LED backed with a heat sink is driven by a driving circuit and controlled by a timing circuit. A temperature monitor can be included in a closed loop to feed back and control the driver. Lenses and/or light guides in the device act to further direct the light.

23 Claims, 6 Drawing Sheets

U.S. PATENT DOCUMENTS

| | | |
|---|---|---|
| 6,116,748 A | 9/2000 | George |
| 6,150,771 A | 11/2000 | Perry |
| 6,159,005 A | 12/2000 | Herold et al. |
| 6,161,910 A | 12/2000 | Reisenauer et al. |
| 6,191,568 B1 | 2/2001 | Poletti |
| 6,200,134 B1 | 3/2001 | Kovac et al. |
| 6,285,139 B1 | 9/2001 | Ghanem |
| 6,296,367 B1 | 10/2001 | Parsons et al. |
| 6,331,111 B1 | 12/2001 | Cao |
| 6,333,602 B1 | 12/2001 | Kayser |
| 6,351,402 B1 | 2/2002 | Carroll |
| 6,419,483 B1 | 7/2002 | Adam et al. |
| 6,611,110 B1 * | 8/2003 | Fregoso ............ 315/224 |
| 6,692,251 B1 | 2/2004 | Logan et al. |
| 6,724,156 B2 * | 4/2004 | Fregoso ............ 315/291 |
| 7,210,930 B2 * | 5/2007 | Kovac et al. ............ 433/29 |
| 2003/0036031 A1 * | 2/2003 | Lieb et al. ............ 433/29 |
| 2003/0219693 A1 | 11/2003 | Cao |
| 2006/0122619 A1 * | 6/2006 | Kablik et al. ............ 606/88 |

OTHER PUBLICATIONS

Hoffart, Fran, Series LED Driver Operates on 3-V Input, Ideas for Design, Dec. 15, 1997, 106 and 108, vol. 2328.

LT1307/LT1307B, Single Cell Micropower 600 kHz PWM DC/DC Converters, Linear Technology Datasheet.

LT1872, Constant Frequency Current Mode Step-up DC/DC Controller in SOT-23, Linear Technology Datasheet.

* cited by examiner

PHOTOPOLYMERIZATION APPARATUS

This application is a continuation-in-part of U.S. patent application Ser. No. 10/647,028, filed Aug. 22, 2003, now abandoned, which was a continuation of U.S. patent application Ser. No. 09/907,140, filed Jul. 17, 2001, now U.S. Pat. No. 6,611,110 B1, which was a continuation-in-part of Ser. No. 09/765,897 filed Jan. 16, 2001, now U.S. Pat. No. 6,724,156 B2. The disclosure of each of these applications are hereby incorporated by reference in their entirety, including all figures, tables and drawings.

BACKGROUND OF THE INVENTION

A number of resins which are cured or polymerized in response to light are known. Perhaps the most familiar of these are resins or composites used in dental technology. Dental composites are used to fill cavities, bond abraded enamel and for many cosmetic applications. When irradiated with light, dental resins polymerize due to a metacrylate based curing mechanism. Photo-initiators, such as camphor quinone and phosphine oxide, start the curing process by absorbing a broad band within the blue spectral range. For example, camphor quinone has an absorption maximum of about 472 nanometers (nm), while phosphine oxide has an absorption maximum of 430 mm.

Light of this wavelength can be generated by tungsten-halogen lamps, laser diodes or light emitting diodes (U.S. Pat. No. 6,159,005). In order to achieve light of sufficient intensity for photopolymerization when using light emitting diodes (LEDs), it is often necessary to employ a plurality of LEDs (U.S. Pat. No. 5,420,768, U.S. Pat. No. 5,634,711 and U.S. Pat. No. 6,102,696). Photocuring devices which utilize a plurality of LEDs consume a great deal of power and produce much heat. This increased energy requirement contributes to the weight and complexity of these devices. Further, complicated systems are needed to capture and focus the light from the multiple LEDs which reduce the efficiency of current devices.

From the foregoing, it is apparent that a light-weight, cool-running and efficient hand-held photocuring device is needed. This device preferably is powered by a self-contained source, for example, a simple battery, so that the device is portable and not encumbered with cords. The device should be light-weight so that it is easily maneuvered during delicate procedures and should run cool so as not to adversely affect the polymerization process by providing excess heat to the photopolymerization reaction.

All patents, patent applications, provisional patent applications and publications referred to or cited herein, are incorporated by reference in their entirety to the extent they are not inconsistent with the explicit teachings of the specification.

SUMMARY OF THE INVENTION

A light-weight, portable photocuring device delivers light of sufficient intensity to cause photopolymerization using a single light emitting diode (LED). The single high powered LED is driven by a driving circuit controlled by a timing circuit. The driving circuit controls the power applied to the LED insuring sufficient power is applied to the LED to achieve an adequate curing intensity. A heat sink on the LED is monitored by a thermal monitor. The device can be powered with a simple low powered alkaline battery or a high powered lithium ion battery. Only continuous current is supplied to the diode, the LED is not pulsed, therefore the life of the diode is preserved. The single LED can be positioned internally within the device or at the tip of the device. When placed internally, a system of one or more lenses and/or known light focusing means or light guides can be added to the device to further focus and intensify the light provided by the LED.

DETAILED DESCRIPTION OF THE INVENTION

Figure 1:
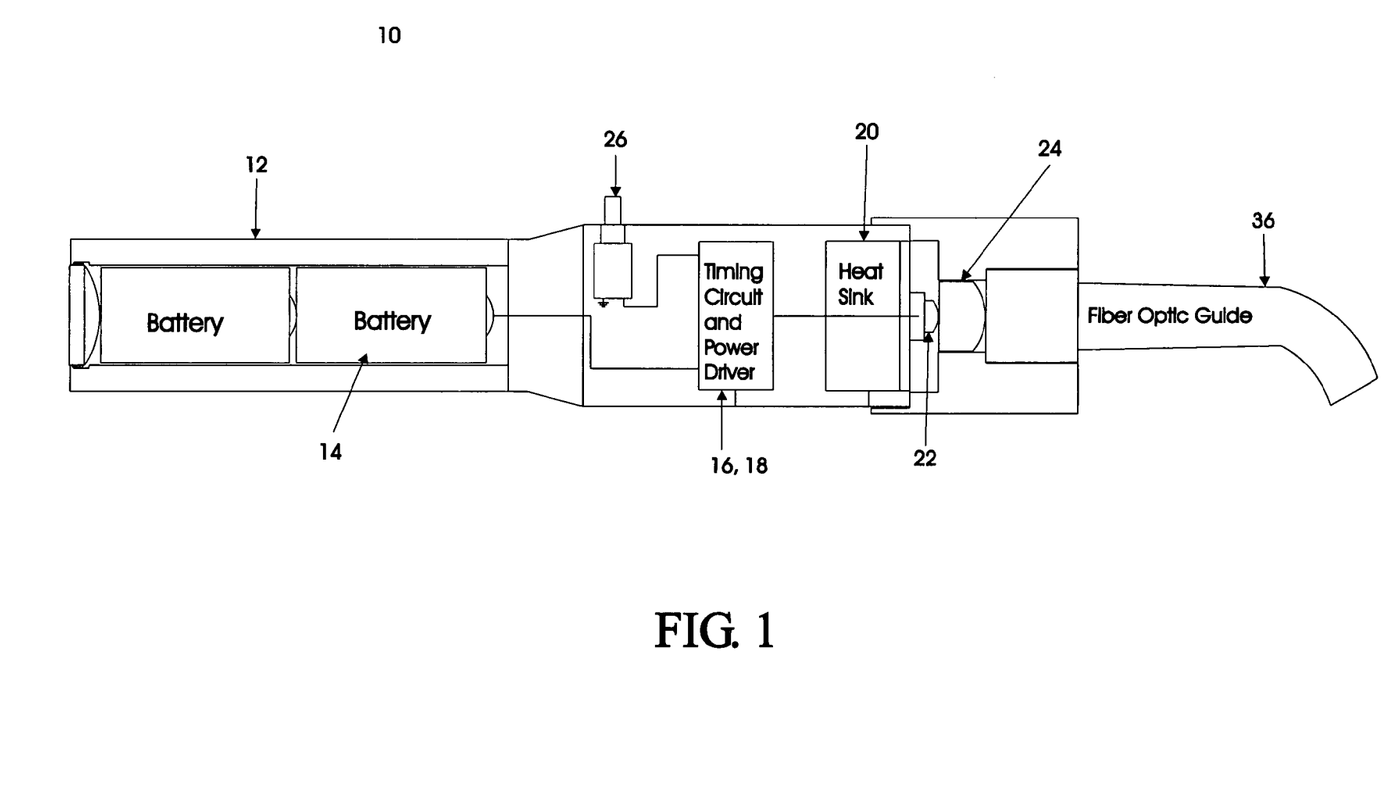
FIG. 1 is a cross-sectional view down the longitudinal axis of a preferred embodiment of the photopolymerization device of the subject invention.

A preferred embodiment of the apparatus of the subject invention is shown generally at 10 in FIG. 1. FIG. 1 shows a hand-held portable photocuring device that utilizes a single light emitting diode (LED). A housing 12 contains a power supply 14, i.e. batteries, a timing circuit 16, and LED power driver 18, a heat sink 20 and single high power LED 22. The housing can also contain, or be fitted with, a lens system 24 for focusing the light from the LED and a light guide 36. A momentary switch 26 can be placed on the exterior of the housing to activate the timing circuit.

The power source 14 provides power to a timing circuit and LED power driver. The power source can be one or more alkaline batteries, or rechargeable batteries, such as lithium ion or nickel metal hydride, or the device can be plugged into a wall socket. Batteries allow full maneuverability of the device because it is not restricted by a cord.

In a preferred embodiment, the timing circuit is an LM 555 timing circuit. This CMOS based timing circuit requires little energy thus applying little draw to the battery and is extremely reliable. A momentary switch 26 starts the timing circuit which is set to run for a period of time. For example, the timing circuit can be set for between about 5 and 10 seconds.

Figure 2:
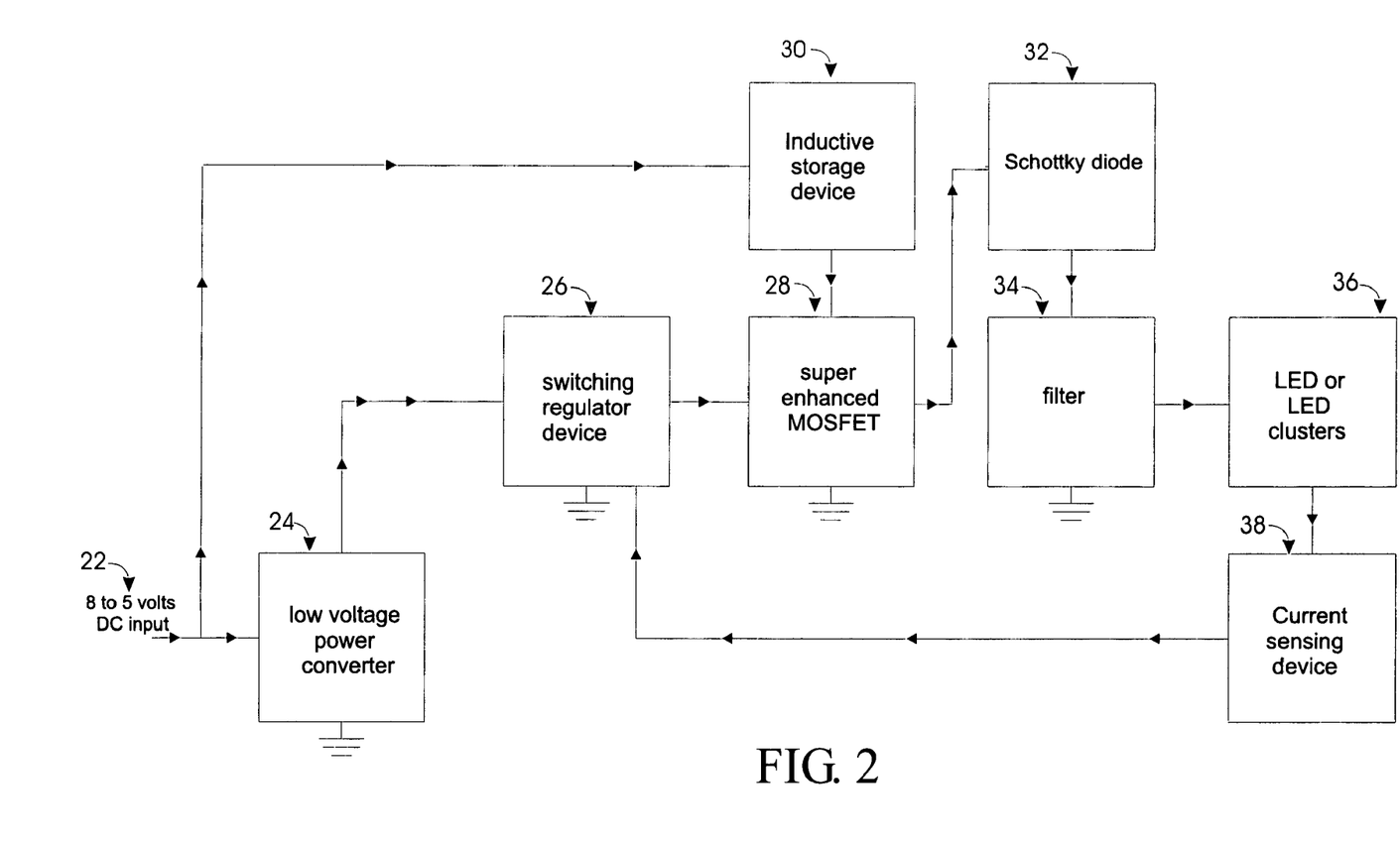
FIG. 2 is a schematic view of a preferred embodiment of the power driver of the photopolymerization device of FIG. 1.

An LED power driver 18 drives the LED 22. This power driver should be highly efficient. In a preferred embodiment, the LED power driver is that described in U.S. patent application Ser. No. 09/765,897, filed Jan. 16, 2001, U.S. publication number US-2002-0014862-A1, published Feb. 7, 2002. Briefly, the driver circuit comprises an inductive storage device 30, a switching regulator device 40, a rectifier 32 and filter 34, a transistor MOSFET and, a current sensing device 38 in a closed loop feedback system (FIG. 2). An inductive storage device allows the LED to be driven with minimal voltage input. Further, the inductive storage device modulates high voltage input allowing the device to take advantage of higher voltage power sources. The switching regulator device monitors and regulates the power applied to the LED, protecting the diode.

In a specific embodiment, a power source provides DC current to an inductive storage device 30, such as an inductor. Preferably, the inductive storage device is wire wound with an inductance between about 18 and 220 micro henries. Wire wound inductors reduce resistance.

Current from the inductive storage device goes to a high speed switching converter and regulator device 40. The switching regulator device can be an integrated circuit (IC) having a reference voltage source, an oscillation circuit, and an error amplifier. In a preferred embodiment the switching regulator device is a CMOS PWM/PFM-control step-up switching regulator. A super enhanced MOSFET 44 loads and collapses the inductive field.

Energy in the inductive storage device is converted to AC current. Energy leaving the switching regulator device is likewise AC current. Accordingly, this AC current can be rectified and filtered to DC current through a rectifier 32 and filter 34. A Schottky diode is a preferred rectifier and filter. A Schottky diode can provide a fast reverse recovery time and a low forward voltage drop. The rectified and filtered current is fed back to the switching regulator device where it can be controlled and monitored for the proper voltage output. In this embodiment, a low power converter 42 supplies the 3V necessary to power the switching regulator device 40.

The rectified and filtered DC output is sent to a current sensing device 38, which controls the current sent to the LED 22. In a specific embodiment, the current sensing device 38 is a low resistance resistor, preferably 1.0 ohm (Ω), or less to minimize loss of efficiency due to heat. The current sensing device in conjunction with the switching regulator device comprises a temperature compensation circuit. The temperature compensation circuit, therefore has an error amplifier, a current sensing resistor, and at least two reference voltage resistors. The current sensing and temperature compensation circuit controls the temperature, protecting the light emitting diode from thermal runaway and allows the LED to be driven at or near maximum current without the LED being destroyed.

Figure 3:
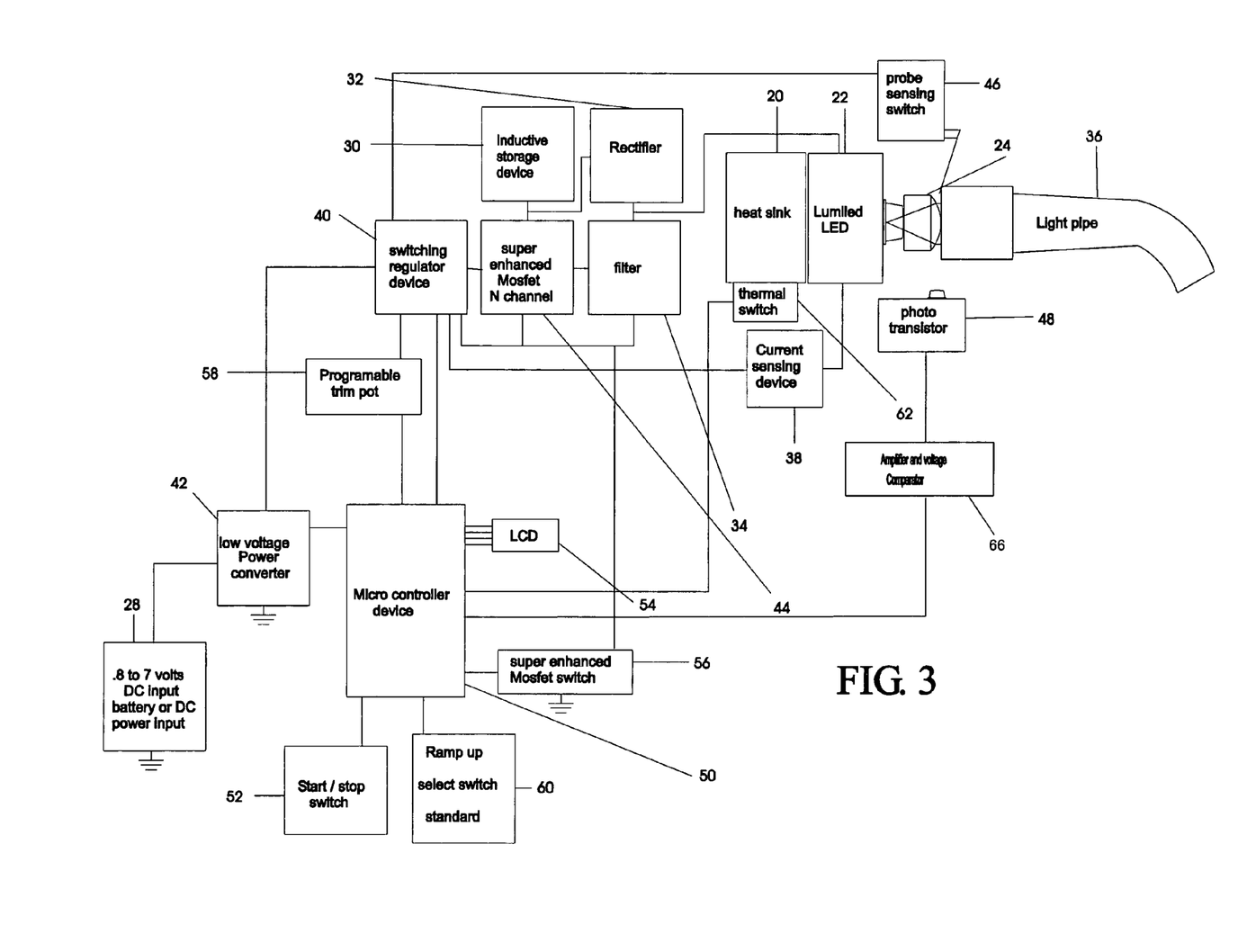
FIG. 3 is a cross-sectional view down the longitudinal axis of another preferred embodiment of the photopolymerization device of the subject invention.

Another specific embodiment of a preferred circuit is shown incorporated into the photocuring device of FIG. 3. In this circuit, the timing circuit is a microcontroller.

The DC power input 28 provides power to the inductive storage device 30. Within the inductive storage device 30 energy is transformed into AC current. The energy is converted from AC to DC current by a rectifier 32. Preferably, the rectifier is a Schottky diode. The current is then filtered at 34 before being applied to the LED 22. A current sensing device 38 feeds a signal reference voltage back to a switching regulator device 40 providing current load information for regulating the circuit. Preferably, the current sensing device 38 is a resistor having a resistance of less than about 15Ω. In a particularly preferred embodiment, the resistor has a resistance of one Ω, or less.

The switching regulator device 40 monitors the signal from the current sensing device 38 and regulates the energy released into the circuit. In a specific embodiment, the switching regulator device 40 requires about 3 V of power. A low voltage power converter circuit 42 is introduced into the circuit to provide the power necessary to run the switching regulator device 40. Preferably, the low voltage power converter is capable of producing 3 V when supplied with as little as 0.8 V input. The converter circuit should further be capable of producing about 20 mA when supplied with the 0.8 V DC input. The low voltage power converter 42 supplies the 3 V necessary to power the switching regulator device 40. The switching regulator device 40 can incorporate a programmable reference voltage source, an oscillation circuit, and an error amplifier. An external super enhance MOSFET 44 is controlled by the switching regulator device 40 and loads the inductive storage device 30. The super enhanced MOSFET is a very efficient transistor and requires very little current to operate. A super enhanced MOSFET 56 acts as the main power switch for the apparatus.

Figure 4:
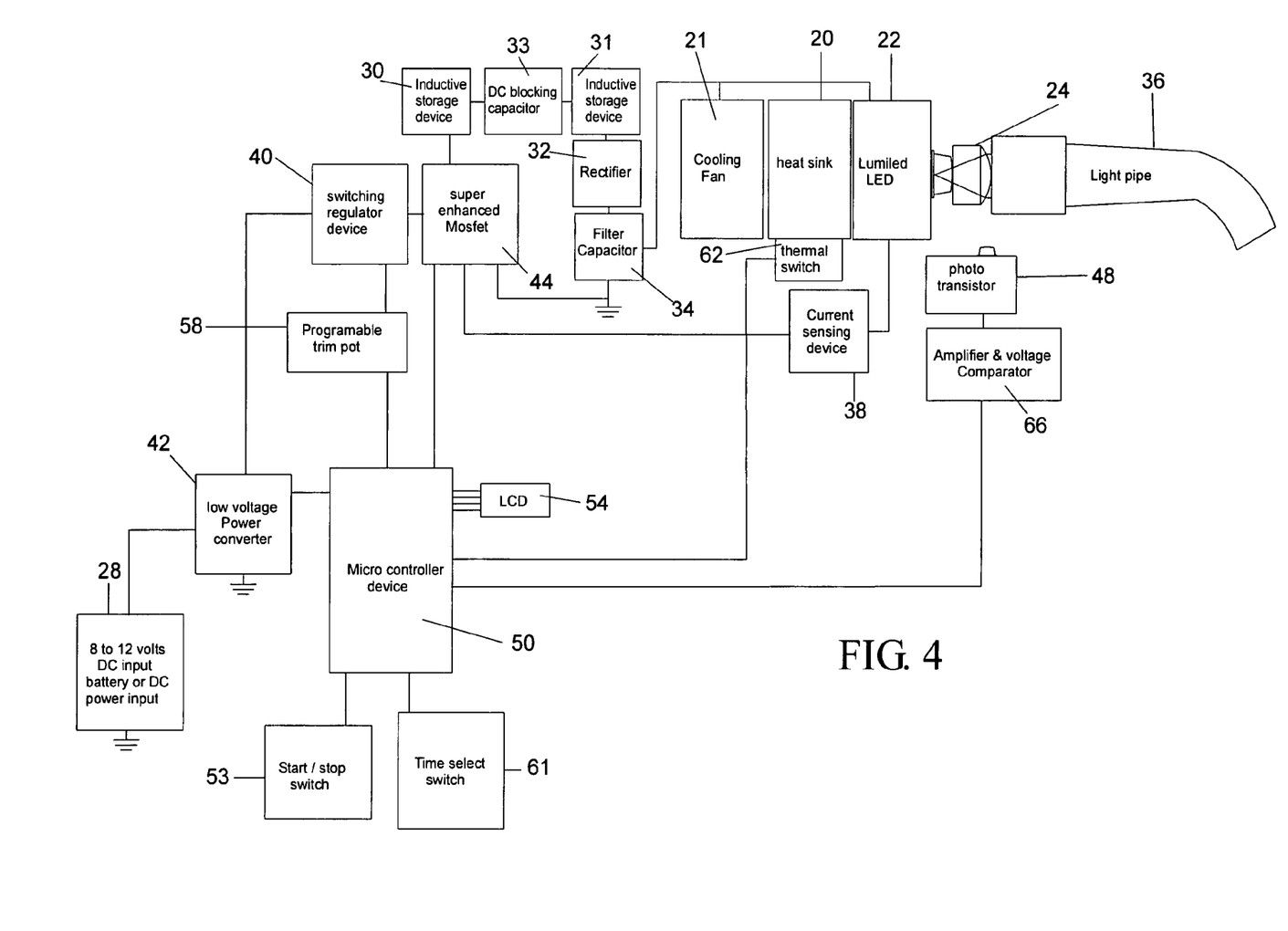
FIG. 4 is a cross-sectional view down the longitudinal axis of another preferred embodiment of the photopolymerization device of the subject invention.
Figure 5:
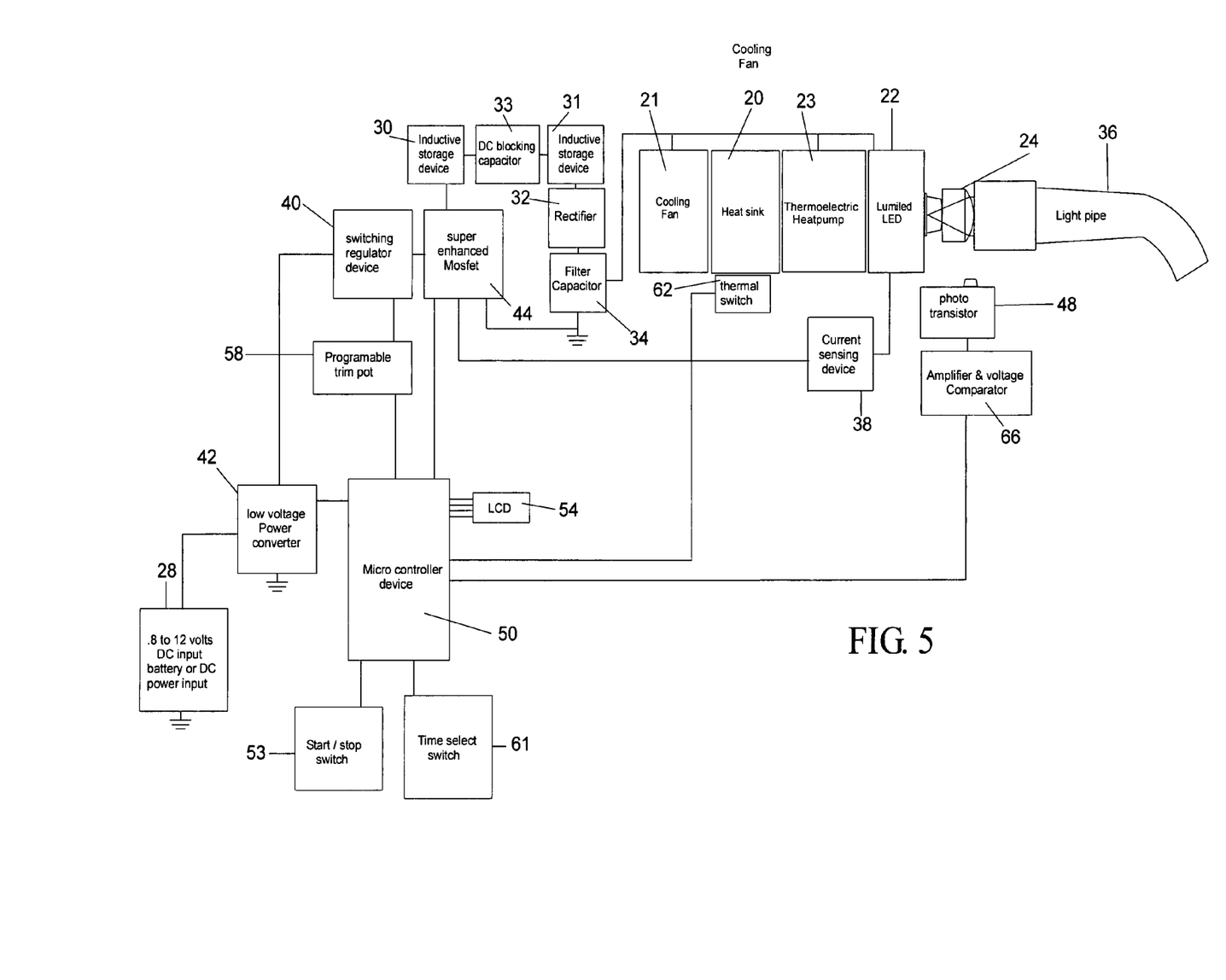
FIG. 5 is a cross-sectional view down the longitudinal axis of another preferred embodiment of the photopolymerization device of the subject invention.

Another specific embodiment of the preferred circuit is shown incorporated into the photocuring device of FIGS. 4 and 5. This circuit can accommodate a greater swing of power input voltages. The circuit modulates the power up or down to a proper current to drive the LED. The up/down converter compensates for battery decay, and preferably is a CMOS PWM PFM control step-up/step-down switching regulator 43. Further, inductive storage device 31 runs in resonance with inductive storage device 30 allowing the circuit to switch to a lower voltage output to accommodate LEDs with a lower forward voltage drop.

Figure 6:
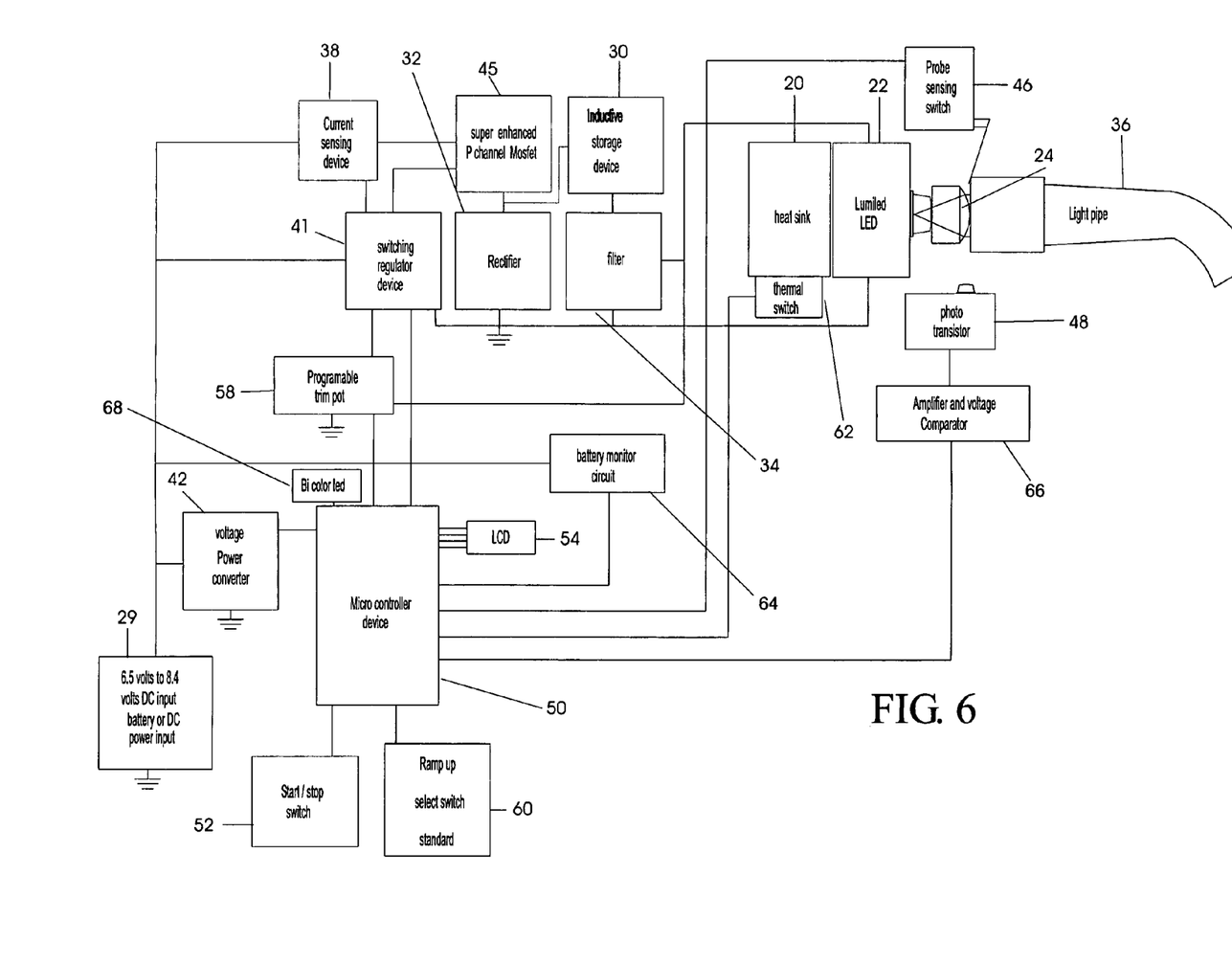
FIG. 6 is a cross-sectional view down the longitudinal axis of another preferred embodiment of the photopolymerization device of the subject invention.

Another specific embodiment of the preferred circuit is shown incorporated into the photocuring device of FIG. 6. This circuit utilizes a higher voltage power sources and modulates the power down to a proper current to drive the LED, preferably 1.25 A. A higher voltage power source allows prolonged curing cycles.

The DC power input 29 provides power to a current sensing device 38. Preferably, the current sensing device 38 is a resistor having a resistance of less than about 15Ω, and most preferably about one Ω, or less minimizing power loss and increasing efficiency therefore prolonging curing cycles. Current flows from the current sensing device to a super enhanced MOSFET 45. The enhanced MOSFET conducts and loads the inductive storage device 30. Within the inductive storage device 30 energy is transformed into AC current. The energy is converted from AC to DC current by a rectifier 32. Preferably, the rectifier is a Schottky diode. The current is then filtered at 34 before being applied to the LED 22. As the LED conducts, the current sensing device 38 feeds a signal reference voltage to a switching regulator device 41 providing current load information for regulating the circuit. In a preferred embodiment the switching regulator device 41 is a CMOS PWM control step-down switching regulator.

The photocuring apparatus of the subject invention further comprises a heat sink 20. Preferably, the heat sink is aluminum. The heat sink can also be other means known in the art of dissipating heat or a combination thereof. For example, in FIG. 4 a cooling fan 21 provides active cooling to the system. A solid state, thermal electric heat pump 23 is combined with a heat sink and cooling fan in the circuit shown in FIG. 5. The cooled LED emits more lumens per watt of power and is therefore more efficient providing more output power for curing.

The light emitting diode used in the apparatus of the subject invention is a high power LED 22. While a conventional LED can withstand a maximum current of 30 mA, a high power LED can withstand a maximum continuous current of about 1.5 A. High powered LEDs have a normal operating current of about 850 mA or 5.5 watts. A specific example of such an LED is a LUMILED Power Light Source. Additionally, the LED used in the exemplified embodiments emits blue light of 470 nm. LEDs emitting other wavelengths of light can be used in the apparatus of the subject invention. For example, light of 430 nm is useful in some dental applications while light in the red spectra is useful for some dermal treatment applications.

Light from the LED can be focused by one or more culminating lenses/reflectors 24 and further guided to the area of polymerization with a light guide 36. A normal LED emits light at an approximately 20° angle. The high powered LEDs used in the apparatus of the subject invention emit light at 120° angle. Thus, a culminating lens is used to focus the emitted light into a narrow, useful, beam path. The lens preferably is in contact with the LED to culminate the light efficiently and minimize loss of light. The lens can be made from glass or a plastic, such as polystyrene. The lens is ground or configured to focus the light emitted at 120° from the light emitting diode into a beam of about 8 mm. Light guides are known in the art and serve to deliver emitted light to the point of photopolymerization. Light guides useful according to the subject invention include a simple, glass or polycarbonate tube. Preferably, the guide should be opaque and be able to be sterilized, most preferably by autoclaving. Therefore, the waveguide tip of the unit can be removed and sterilized between patients. Other known waveguides include those having fiber optic bundles to direct emitted light to the tip of the device. Preferably, the light guide is in contact with the lens to further minimize loss of light. Additionally, the LED can be placed at the tip of the instrument so the light can be delivered directly to the surface of the tooth.

The specific embodiment of the photopolymerization device shown in FIGS. 3 and 4 further include features which enhance the safety and utility of the subject device. For example, a microcontroller 50 replaces the timing circuit of the device shown in FIG. 1. The microcontroller 50 times the illumination period for curing providing a selection of times, for example, from 5 seconds incrementally to 40 seconds, selected by the curing time select switch 60 and noted by a liquid crystal display (LCD) 54.

A probe sensing switch 46 acts as a safety switch wherein the device delivers maximum intensity only when the wave guide 36 is seated on the culminating lens 24. A thermal switch 62 embedded in the heat sink provides feedback to the microcontroller 50 preventing the LED from overheating.

A phototransistor 48 measures stray light to determine if the device is providing adequate light output. The phototransistor 48 acts as a simple radiometer operating at a preset valve. An amplifier and voltage comparator 66 conditions and amplifies the signal into a digital format to be analyzed and fed to the microcontroller 50. Thus, the phototransistor 48 acts as a secondary back-up. The current sensing device assures the LED is receiving proper current while the phototransistor assures the apparatus is delivering light of sufficient intensity. Should the LED begin to degrade, the phototransistor sends a signal to the microcontroller 50 which will shut the device down and indicate an error.

Combination of the microcontroller 50 and a programmable trim pot 58 allow adjustment of the output intensity of light. A select switch 60 allows the user to choose full power immediately or to have the power ramp up from, for example, 0 to full power in a number of seconds. LED indicator lights can be installed on the select switch 60 to indicate the power selection. Likewise, audible signals can be provided indicating, for example, the start, one beep, and the finish two beeps of the curing cycle. The curing cycle is started upon activation of a start/stop switch 52. In an alternative embodiment shown in FIGS. 4 and 5 a start/stop switch 53 is used with a time select switch 61 to allow the user to specify the desired duration of the curing time.

The battery monitor circuit 64 monitors battery decay and digitizes data for interpretation by the microcontroller 50. The microcontroller sends the information to a bicolor LED 68 and the LCD 54. The bicolor LED gives a visual indication of battery status.

It is noted that previous devices employing a plurality of LEDs require much power to operate. The LEDs in these devices must be pulsed to achieve sufficient light intensity. The device of the subject invention employs an efficient circuit that provides direct current to the single LED. Because this LED is not pulsed, it is not stressed and therefore the circuit of the device of the subject invention contributes to the longevity of the LED.

Utilizing a high powered LED in the device of the subject invention allows that only a single LED need be present in the device. In preferred embodiments, this LED is driven by circuits which supply continuous current to the LED. Application of continuous current reduces stress on the diode assuring its longevity. The LED could however be pulsed and deliver sufficient light. One skilled in the art is aware of how to convert a circuit to a pulsing circuit. Preferably, any pulsing circuit would have a current sensing device and perhaps a phototransistor to protect the LED and detect its eminent degradation.

It is estimated that between 4 and 6 percent of emitted light is lost with the addition of each lens to an LED. A lens captures and directs that light into an intensified useable beam. Prior devices which utilize a plurality of LEDs require a plurality of lenses. Much light is lost in these devices greatly reducing their efficiency. The device of the subject invention however utilizes only a single LED. The light from this LED can be focused using a single lens making the subject device far more efficient than those requiring multiple lights and lenses.

The simple, efficient driving circuit requires little energy to operate and provides sufficient power to drive a single high powered LED to the photocuring device of the subject invention. Further, only light emitted from a single LED must be focused within the subject device, thus little light is lost or wasted.

It should be understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. A photopolymerization apparatus comprising:
a housing;
one light emitting diode;
a heat sink;
a timing circuit that is a microcontroller;
a driver circuit, wherein said driver circuit comprises one inductive storage device, a DC blocking capacitor, another inductive storage device, a switching regulator device, a rectifier, a filter, a current sensing device, and a transistor MOSFET; and
a means for applying power to said driver circuit, wherein the another inductive storage device runs at resonance with the one inductive storage device.

2. The apparatus of claim 1, wherein said inductive storage device is wire wound with an inductance between about 18 and 220 micro henries.

3. The apparatus of claim 1, wherein said switching regulator device comprises:
a programmable reference voltage source;
an oscillation circuit; and
an error amplifier.

4. The apparatus of claim 1, wherein said switching regulator device is a CMOS PWM PFM switching regulator.

5. The apparatus of claim 1, wherein said rectifier is a Schottky diode.

6. The apparatus of claim 1, wherein said current sensing device and said switching regulator device are a temperature compensation circuit comprising an error amplifier, a current sensing resistor and at least two reference voltage resistors.

7. The apparatus of claim 1, wherein said transistor MOSFET is super enhanced.

8. The apparatus of claim 1, further comprising a low voltage power converter circuit.

9. The apparatus of claim 8, wherein said low voltage power converter circuit produces 3 volts and 20 milliamps when supplied with at least 0.8 volts input.

10. The apparatus of claim 1, wherein said means for applying power is at least one battery.

11. The apparatus of claim 1, further comprising at least one lens/reflector.

12. The apparatus of claim 11, wherein said at least one lens/reflector contacts said one light emitting diode.

13. The apparatus of claim 1, further comprising a light guide.

14. The apparatus of claim 1, further comprising at least one lens and a light guide.

15. The apparatus of claim 1, further comprising a phototransistor for detecting stray light and providing feed back to said microcontroller.

16. The apparatus of claim 1, further comprising a thermal switch which feeds back to said microcontroller.

17. The apparatus of claim 1, further comprising a programmable trim pot to allow power to be ramped up.

18. The apparatus of claim 1, further comprising an enhanced MOSFET to detect leakage current.

19. The apparatus of claim 1, further comprising a start/stop switch.

20. The apparatus of claim 1, further comprising and liquid crystal display as a visual display.

21. The apparatus of claim 1, further comprising a battery monitor circuit.

22. The apparatus of claim 1, further comprising a cooling fan.

23. The apparatus of claim 1, further comprising a solid state thermal electric heat pump.

\* \* \* \* \*